United States Patent [19]

Iijima et al.

[11] 4,226,915

[45] Oct. 7, 1980

[54] PRESSURE-SENSITIVE ADHESIVE TAPE OR SHEET

[75] Inventors: Eiji Iijima, Sakura; Yoshimi Nishimura, Funabashi, both of Japan

[73] Assignee: Kao Soap Co., Ltd., Tokyo, Japan

[21] Appl. No.: 957,083

[22] Filed: Nov. 2, 1978

[30] Foreign Application Priority Data

Nov. 16, 1977 [JP] Japan ................................ 52-138281

[51] Int. Cl.³ ............................................ B32B 25/04
[52] U.S. Cl. .................................... 428/492; 428/500; 428/511; 428/514; 428/521; 428/522; 428/523
[58] Field of Search ................ 427/207; 428/492, 500, 428/511, 514, 521, 522, 523

[56] References Cited

U.S. PATENT DOCUMENTS 3,632,740  1/1972  Robinson ....................... 427/207 X

FOREIGN PATENT DOCUMENTS 49-97059 12/1974 Japan .
50-49336 11/1975 Japan .

*Primary Examiner*—Bernard D. Pianalto
*Attorney, Agent, or Firm*—Blanchard, Flynn, Thiel, Boutell & Tanis

[57] ABSTRACT

A pressure-sensitive adhesive tape or sheet comprising an air-permeable substrate having coated thereon, an adhesive composition comprising (a) 3 to 25% by weight of a water-soluble polyol and (b) 1 to 25% by weight of a water-soluble or water-swellable polymer, the sum of the contents of the components (a) and (b) being at least 6% by weight, with the balance of the adhesive composition being an adhesive.

7 Claims, No Drawings

PRESSURE-SENSITIVE ADHESIVE TAPE OR SHEET

BACKGROUND OF THE INVENTION

1. Field of the Invention

The present invention relates to a pressure-sensitive adhesive tape or sheet. More particularly, the invention relates to a pressure-sensitive adhesive tape or sheet which is moisture permeable and which scarcely causes an eruption (skin lesion) or irritation of the skin when it is applied on the skin for a long time.

2. Description of the Prior Art

Various polymeric compounds have heretofore been used as adhesives for pressure-sensitive adhesive tapes or sheets. For example, there can be mentioned copolymers comprising an alkyl acrylate as the main component, vinyl acetate-ethylene copolymers, natural rubbers, sulfur-cross-linked natural rubbers and polyisoprenes. Pressure-sensitive adhesive tapes and sheets which possess excellent properties, such as adhesiveness and weatherability, are prepared and used in various fields. However, when these adhesive tapes or sheets are used on the human body, i.e., as bandages or wrappings, they readily cause eruption or irritation of the skin. Elimination of this defect has been eagerly desired.

Japanese Patent Publication (Kokai) No. 97059 of 1974 discloses an air-permeable pressure-sensitive tape coated with an adhesive composition consisting of 90–99% by weight of a copolymer, a primary component of which is an alkyl acrylate having an alkyl radical of at least 4 carbon atoms, and 10–1% by weight of hydroxyethyl cellulose.

Japanese Patent Pubilication (Kokai) No. 49336 of 1975 discloses an air-permeable pressure-sensitive tape or sheet coated with an adhesive composition consisting of:

(A) 90–99% by weight of a copolymer consisting of 85–99% by weight of an alkyl acrylate having an alkyl radical of at least 4 carbon atoms, and 1–15% by weight of a compound copolymerizable with said alkyl acrylate, and (B) 10–1% by weight of hydroxyethyl cellulose.

It has been considered that the causes of skin eruption or irritation resulting from the use of adhesive plasters include a physical cause, namely, the damage of the horny layer of the skin surface caused by peeling of the tape or the like from the skin surface, a chemical cause, namely, a primary irritation by or an allergic reaction to the adhesive, and a physiological cause, namely, inhibition of the evaporation of water (skin respiration) caused by blocking of the sweat openings on the skin surface. Among these causes, the physiological cause is most serious. More specifically, a pressure-sensitive adhesive tape or sheet is poor in air permeability, moisture permeability and/or moisture absorbing property. When it is applied to the skin, it causes clogging of sweat openings on the skin surface. It is considered that this action is a main cause of skin eruption or irritation resulting from the use of adhesive plasters. As a means for eliminating this defect, there has been proposed a method in which fine apertures are formed in the pressure-sensitive adhesive tape or sheet, which apertures extend through the adhesive layer thereof. In a pressure-sensitive adhesive tape or sheet prepared according to this method, however, although the aperture portions provide air permeability and moisture permeability, other portions of the tape or sheet are still in the closed or impervious state and hence, the effect of preventing skin eruption or irritation is insufficient. Further, from the technical veiwpoint, this method is still disadvantageous in that the formation of the required fine apertures is quite difficult in the case of an adhesive plaster having a substantial thickness, particularly a thick adhesive layer.

SUMMARY OF THE INVENTION

We have performed research with a view to eliminating the foregoing defects of conventional pressure-sensitive adhesive tapes or sheets. Based on the concept that these defects can be overcome if the entire surface is rendered air-permeable and moisture-permeable, instead of forming discrete, air-permeable, moisture-permeable or moisture-absorbing aperture portions through the tape or sheet, we discovered that when a polymeric adhesive is properly combined with (1) a water-soluble or water-swellable polymer and (2) a water-soluble polyol, there is obtained a pressure-sensitive adhesive tape or sheet having an adhesiveness favorably comparable to that of conventional pressure-sensitive adhesive tape and sheet products, and also having the highly advantageous property that water excreted from the skin can easily be absorbed or allowed to permeate therethrough and hence, skin eruption or irritation is scarcely caused. Based on this finding, we have now completed the present invention.

When a water-soluble polyol, such as glycerin, propylene glycol or the like, is incorporated into an adhesive layer, it is possible to impart moisture permeability to a pressure-sensitive adhesive tape or sheet. However, in the case of a mixture of an adhesive and a water-soluble polyol, the film-forming property is poor, and even if a film is formed, the water-soluble polyol, such as glycerin or propylene glycol, exudes from the film. To our great surprise, it was found that this defect can be effectively eliminated if a water-soluble or water-swellable polymer is uniformly incorporated into the above mixture, and that a homogeneous adhesive layer possessing an excellent film-forming property can be obtained. This adhesive layer also possesses an excellent adhesive effect and it scarcely causes skin eruption or irritation when applied to the skin. In contrast, if a monohydric alcohol is used instead of the moisture-permeable water-soluble polyol, the moisture permeability of the adhesive layer is degraded because of the volatile characteristic in the case of methanol, ethanol and propanol, and in case of butanol, because of an insufficient hydrophilic characteristic thereof (solubility=9.1 ml per 100 ml of water). Thus, the agent for imparting moisture-permeability to the adhesive layer should be miscible with water at an optional ratio and it should have a low volatility. Moreover, when a water-soluble or water-swellable polymer along is incorporated in an adhesive, a small moisture permeability can be imparted to the adhesive layer, but even if such a polymer is incorporated in a large quantity, an adhesive layer having a good moisture permeability cannot be obtained. Further, when a water-insoluble polymer is used as the polymer for holding the agent for increasing moisture permeability, the holding effect is low because of the poor compatibility thereof with the agent for imparting moisture permeability.

The characteristic feature of the present invention resides in a pressure-sensitive adhesive tape or sheet comprising an adhesive layer containing an adhesive, a water-soluble polyol and a water-soluble or water-swellable polymer. More specifically, the adhesive layer comprises a homogeneous mixture containing 3 to 25% by weight of a water-soluble polyol and 1 to 25% by weight of a water-soluble or water-swellable polymer, wherein the sum of the amounts of the water-soluble polyol and the water-soluble or water-swellable polymer is at least 6% by weight, with the balance of the adhesive layer being an adhesive. This pressure-sensitive adhesive tape or sheet is advantageous in comparison with the conventional pressure-sensitive adhesive tapes or sheets in the following points. Namely, the step of forming fine apertures in the tape or sheet can be omitted, and the loss of the starting materials by formation of fine apertures therein is prevented. Moreover, since this tape is applied in an open state allowing evaporation of water, it scarcely causes skin eruption or irritation.

Polymeric compounds heretofore commonly used in this field can be used as the adhesive component of the adhesive layer in the present invention. However, in view of the fact that the intended purpose of the present invention cannot be attained unless the adhesive layer is coated on a substrate in a homogeneously mixed state, it is preferred that the adhesive component be used in such form that the other two hydrophilic components of the adhesive layer can easily be incorporated therein to form a homogeneous mixture, namely, in the form of an aqueous latex. For example, there are preferably employed aqueous latices of natural adhesives such as natural rubbers, grafted natural rubbers and cross-linked natural rubbers and synthetic adhesives such as polyisoprenes, grafted polyisoprenes, poly(alkyl acrylates) having 1 to 10 carbon atoms in the alkyl moiety, copolymers of vinyl acetate with an alkyl acrylate having 1 to 10 carbon atoms in the alkyl moiety and vinyl acetate-ethylene copolymers. When these polymers are used in the form of water-based latices, it is preferred that the latices contain 40 to 60% of the polymers as the solids.

The water-soluble polyols that are used as the agent for imparting moisture permeability in the present invention include, for example, propylene glycol, glycerin, butylene glycol, hexylene glycol, polyethylene glycols having a molecular weight not higher than 1,000, ethylene glycol, polypropylene glycol having a molecular weight of up to 1,000, mannitol and sorbitol. It is critical that the agent for imparting moisture permeability is contained in the adhesive layer in an amount of 3 to 25% by weight. When the amount of the water-soluble polyol is less than 3% by weight, the moisture permeability of the adhesive layer is insufficient. When the amount of the water-soluble polyol is more than 25% by weight, the adhesiveness of the adhesive layer is degraded and peeling readily occurs.

The water-soluble or water-swellable polymer that is used in the present invention for holding the water-soluble polyol include, for example, polyvinyl alcohol, methyl cellulose, hydroxyethyl cellulose, hydroxypropyl cellulose, carboxymethyl cellulose, sodium alginate and polyethylene oxides having a molecular weight higher than 300,000. It is critical that such water-soluble or water-swellable polymer is contained in the adhesive layer in an amount of 1 to 25% by weight. In order to attain a complete moisture permeability, it is critical that the sum of the amounts of the water-soluble polyol and the water-soluble or water-swellable polymer is at least 6% by weight, based on the total weight of the adhesive layer.

In the case of an adhesive plaster for obtaining certain pharmaceutical effects, such pharmaceutical components as pepper extract, methyl salicylate, l-menthol and camphor can be incorporated into the adhesive layer.

In the present invention, the thickness of the adhesive layer is determined according to the intended use of the pressure-sensitive adhesive tape or sheet. In general, the thickness of the adhesive layer is in the range of 50 to 2,000 g/m$^2$, preferably 150 to 1,000 g/m$^2$.

Air-permeable substrates are used as the substrate of the pressure-sensitive adhesive tape or sheet according to the present invention. For example, any materials such as papers, fabrics, non-woven fabrics and finely perforated plastic films can be used. A commercially available release paper can be used to provide a removable covering for the adhesive layer of the pressure-sensitive adhesive tape or sheet of the present invention. A silicone-treated cellophane paper or plastic film, which can easily be released, is preferably used.

The pressure-sensitive adhesive tape or sheet of the present invention can be prepared according to any of the customary manufacturing methods. For example, the pressure-sensitive adhesive tape or sheet of the present invention can be prepared according to the following method.

An adhesive (in the form of a latex) is homogeneously mixed with an aqueous solution or dispersion of the water-soluble or water-swellable polymer, and the water-soluble polyol is added to the homogeneous mixture and is mixed uniformly therein. A pharmaceutical ingredient such as camphor or methyl salicylate, can optionally be added according to need. The resulting liquid mixture is cast on a substrate such as a cotton fabric and is dried whereby to form a filmy adhesive layer.

The pressure-sensitive adhesive tape or sheet prepared according to the present invention can advantageously be applied to the same uses for which the conventional products have heretofore been employed. When this tape or sheet is used as a medical tape or sheet, especially good results can be obtained and a high effect of preventing skin eruption or irritation can be attained.

As will be apparent from the foregoing description, according to the present invention, there can be provided a pressure-sensitive adhesive tape or sheet having a high water permeability, which scarcely causes skin eruption or irritation even if it is applied to the skin for a long time.

The present invention will now be described in more detail by reference to the following illustrative Examples which do not limit the scope of the invention.

EXAMPLE 1

An aqueous emulsion of a polymer (having a solid content of 60% by weight), in which the polymer was a copolymer of 80 parts by weight of 2-ethylhexyl acrylate and 20 parts by weight of methyl methacrylate, was mixed with hydroxyethyl cellulose (commercially available under the trademark "Natrosol 250HR") or polyvinyl alcohol (commercially available under the trademark "Gosenol GM-14"), and glycerin was added to the mixture. The mixture was agitated to form a homogeneous liquid composition. The liquid composition was cast on a cotton fabric and was dried to form a pressure-sensitive adhesive sheet.

In this Example and all of the subsequent Examples, the thickness of the adhesive layer was adjusted to 250 g/m², unless otherwise indicated.

The moisture permeability was determined according to the following method. Method of Determination of Moisture Permeability:

Into a glass bottle having a capacity 50 ml (the mouth diameter being 1.5 cm) was charged 5.0 g of anhydrous calcium chloride, and the mouth of the bottle was sealed with the pressure-sensitive adhesive sheet. The glass bottle was placed in a constant-temperature constant-humidity bath maintained at a temperature of 40° C. and a relative humidity of 90% and allowed to stand for 24 hours. Then, the increase of the weight of calcium chloride was precisely measured (in the unit of mg), and the moisture permeability was expressed in terms of the increase of the weight of calcium chloride. The results obtained are shown in Table 1.

Table 1

| Adhesive (Copolymer) (% by weight) | Water-Soluble or Water-Swellable Polymer | | Moisture-Permeable Agent Glycerin (% by weight) | Moisture Permeability |
|---|---|---|---|---|
| | Hydroxyethyl cellulose (% by weight) | Polyvinyl alcohol* (% by weight) | | |
| 97 | 3 | 0 | 0 | 34 |
| 94 | 6 | 0 | 0 | 40 |
| 91 | 9 | 0 | 0 | 40 |
| 88 | 12 | 0 | 0 | 46 |
| 82 | 3 | 0 | 15 | 110 |
| 79 | 6 | 0 | 15 | 117 |
| 76 | 9 | 0 | 15 | 132 |
| 73 | 12 | 0 | 15 | 140 |
| 92 | 0 | 8 | 0 | 34 |
| 84 | 0 | 16 | 0 | 49 |
| 76 | 0 | 24 | 0 | 46 |
| 68 | 0 | 32 | 0 | 47 |
| 77 | 0 | 8 | 15 | 114 |
| 69 | 0 | 16 | 15 | 127 |
| 61 | 0 | 24 | 15 | 144 |
| 53 | 0 | 32 | 15 | 164 |

Note:
*GM-14 manufactured by Nippon Gosei Kabushiki Kaisha, degree of polymerization = 1000, degree of saponification = 87%

A mixture of the adhesive and the water-soluble or water-swellable polymer was insufficient in the moisture permeability. When glycerin was added to this mixture, a good moisture-permeating effect was obtained for the first time.

EXAMPLE 2

A pressure-sensitive adhesive sheet was prepared by using a copolymer composed of 80 parts by weight of 2-ethylhexyl acrylate and 20 parts by weight of methyl methacrylate, polyvinyl alcohol and glycerin, and this pressure-sensitive adhesive tape was compared with commercially available adhesive plaster M with respect to the adhesive force and moisture permeability. Method of Determination of Adhesive Force:

A specimen having a width of 3.0 cm and a length of 10.0 cm was cut from the pressure-sensitive adhesive sheet, and it was pressed and bonded to an acrylic plate under a pressure of 2.5 Kg/150 cm² for 20 minutes.

One end portion having a length of 0.5 cm of the specimen was peeled from the acrylic plate and was connected to a spring-type suspension balance. The balance was horizontally fixed and the acrylic plate was moved at a speed of 16 m/min in a direction away from the balance to peel the specimen from the acrylic plate.

The load required to effect peeling under these conditions was read from the balance and is designated as the adhesive force. The unit of adhesive force is gram per 3 cm.

The results of the measurements of the moisture permeability and adhesive force are shown in Table 2.

Table 2

| Adhesive Layer Components (% by weight) Copolymer Adhesive (Acrylic acid derivative) | Polyvinyl alcohol | Glycerin | Adhesive Force | Moisture Permeability | Remarks |
|---|---|---|---|---|---|
| 100 (Control) | 0 | 0 | 220 | 12 | exudation of glycerin |
| 80 (Control) | 0 | 20 | — | — | |
| 80 (Control) | 20 | 0 | 210 | 46 | |
| 98 (Control) | 1 | 1 | 215 | 21 | |
| 96 (Control) | 1 | 3 | 200 | 41 | |
| 90 (Invention) | 2 | 4 | 210 | 72 | |
| 70 (Invention) | 7 | 23 | 210 | 124 | |
| 70 (Invention) | 15 | 15 | 225 | 127 | |
| 70 (Invention) | 23 | 7 | 180 | 80 | |
| 50 (Invention) | 25 | 25 | 140 | 112 | |
| 40 (Control) | 30 | 30 | 25 | 125 | |
| substrate (cotton fabric alone) | | | | 252 | |
| commercially available adhesive plaster M | | | 180 | 12 | |

When the adhesive layer contains both polyvinyl alcohol and glycerin so that the sum thereof is at least 6% by weight and the content of each thereof is not higher than 25% by weight, there can be obtained a pressure-sensitive adhesive sheet having an adhesiveness comparable to that of the commercially available adhesive plaster M and a moisture permeability higher than that of the commercially available adhesive plaster M.

EXAMPLE 3

In 133 parts by weight of an aqueous emulsion of a copolymer (having a solid content of 60% by weight), wherein the copolymer is a copolymer of 80 parts by weight of 2-ethylhexyl acrylate and 20 parts by weight of methyl methacrylate, were incorporated 5 parts by weight of polyvinyl alcohol and 5 parts by weight of propylene glycol, and a pressure-sensitive adhesive sheet was prepared by using this mixture. The adhesive force of the thus-prepared sheet was 207 and the moisture permeability of the sheet was 92.

EXAMPLE 4

In 160 parts of an aqueous emulsion of a copolymer (having a solid content of 50% by weight), wherein the copolymer is a copolymer of 70 parts of vinyl acetate and 30 parts of ethylene, were incorporated 5 parts of polyvinyl alcohol and 15 parts of glycerin, and a pressure-sensitive adhesive tape was prepared from this mixture in the same manner as in the preceding Examples. The moisture permeability of the tape was 112 and the adhesive force of the tape was 187.

EXAMPLE 5

In the same manner as described in the preceding Examples, a pressure-sensitive adhesive tape was prepared from 100 parts of an acrylic acid-grafted natural rubber latex ("Resitex ®" manufactured by Nanyo Kasei K.K.; solid content=55% by weight), 7 parts of polyvinyl alcohol and 10 parts of glycerin.

The moisture permeability of the tape was 126 and the adhesive force of the tape was 265.

EXAMPLE 6

5 parts of polyvinyl alcohol and 7 parts of glycerin were homogeneously mixed with 100 parts of an acrylic acid-grafted natural rubber latex (having a solid content of 55% by weight), and the water content was adjusted so that the amount of the coated layer after drying was 500 g/m$^2$. From this composition, a pressure-sensitive adhesive sheet was prepared.

The moisture permeability of the sheet was 181 and the adhesive force of the sheet was 248.

EXAMPLE 7

8 parts of polyvinyl alcohol and 8 parts of glycerin were homogeneously mixed with 100 parts of an aqueous emulsion of a polymer (having a solid content of 50% by weight), wherein the copolymer is a copolymer of 80 parts by weight of 2-ethylhexyl acrylate and 20 parts by weight of methyl methacrylate. The water content was adjusted so that the amount of the coated layer after drying was 1200 g/m$^2$. From this composition, a pressure-sensitive sheet was prepared.

The moisture permeability of the adhesive sheet was 184 and the adhesive force of the sheet was 184.

EXAMPLE 8

5 parts of polyvinyl alcohol and 10 parts of glycerin were added to 50 parts of an aqueous emulsion of a copolymer (having a solid content of 60%) composed of 80 parts of 2-ethylhexyl acrylate and 20 parts of methyl methacrylate and 60 parts of an aqueous emulsion of a copolymer (having a solid content of 50%) composed of 70 parts of vinyl acetate and 30 parts of ethylene, and an adhesive plaster sample was prepared from this composition in the same manner as described in the preceding Examples.

The moisture permeability of the resulting adhesive plaster was 128 and the adhesive force of the plaster was 189.

EXAMPLE 9

An adhesive plaster sample was prepared from 117 parts of an aqueous emulsion of a copolymer (having a solid content of 60% by weight) composed of 80 parts by weight of 2-ethylhexyl acrylate and 20 parts by weight of methyl methacrylate, 15 parts of polyvinyl alcohol and 15 parts of sorbitol.

The moisture permeability of the resulting adhesive sheet was 108 and the adhesive force was 161.

EXAMPLE 10

The product of the present invention was compared with a typical commercially available pressure-sensitive adhesive sheet (having no substantial moisture permeability) with respect to the effects thereof on the applied skin.

Test Method:

The product of the present invention and the commercial pressure-sensitive adhesive sheet were cut into specimens having a size of 4 cm × 3 cm. The specimens were applied to the skin on the top portion of the left and right shoulder blades on the backs of 10 healthy men and they were allowed to remain for 24 hours. After 24 hours had passed, the specimens were peeled, and when another two hours had passed, the conditions of the specimen-applied skins were examined and evaluated according to the following scale.

Evaluation Scale:
−: no change was observed
±: slight red spots were observed
+: strong red spots were observed The results obtained are shown in Table 3. The product of the present invention used in this test was the adhesive tape prepared in Example 4.

Table 3

| Sample | Skin Conditions (number of men) | | |
|---|---|---|---|
| | − | ± | + |
| Product of Present Invention | 10 | 0 | 0 |
| Commercial Product A | 2 | 8 | 0 |
| Commercial Product B | 5 | 4 | 1 |

The embodiments of the invention in which an exclusive property or privilege is claimed are defined as follows:

1. A pressure-sensitive adhesive tape or sheet, comprising an air-permeable substrate having coated thereon a layer of an adhesive composition, said adhesive composition consisting essentially of a substantially homogeneous mixture of (a) 3 to 25% by weight of a water-soluble polyol selected from the group consisting of glycerin, propylene glycol, butylene glycol, hexylene glycol, polyethylene glycols having a molecular weight not higher than 1000, ethylene glycol, polypropylene glycol having a molecular weight of up to 1000, mannitol and sorbitol, (b) 1 to 25% by weight of a water-soluble or water-swellable polymer selected from the group consisting of polyvinyl alcohol, methyl cellulose, hydroxyethyl cellulose, hydroxypropyl cellulose, carboxyethyl cellulose, sodium alginate and polyethylene oxides having a molecular weight higher than 300,000, the sum of amounts of the components (a) and (b) being at least 6% by weight, based on the weight of the adhesive composition, and the balance of the adhesive composition essentially is a pressure-sensitive adhesive capable of adhering to and safe for use on 2. A pressure-sensitive adhesive tape or sheet as claimed in claim 1 wherein said adhesive is a member selected from the group consisting of natural rubbers, grafted natural rubbers and cross-linked natural rubbers.

3. A pressure-sensitive adhesive tape or sheet as claimed in claim 1 wherein said adhesive is a member selected from the group consisting of polyisoprenes and grafted polyisoprenes.

4. A pressure-sensitive adhesive tape or sheet as claimed in claim 1 wherein said adhesive is a member selected from the group consisting of poly(alkyl acrylates) having 1 to 10 carbon atoms in the alkyl moiety, copolymers of vinyl acetate with an alkyl acrylate having 1 to 10 carbon atoms in the alkyl moiety and vinyl acetate-ethylene copolymers.

5. A pressure-sensitive adhesive tape or sheet as claimed in claim 1 wherein the water-soluble polyol (a) is glycerin, the water-soluble or water-swellable polymer (b) is polyvinyl alcohol, and the adhesive is a member selected from the group consisting of poly(alkyl acrylates) having 1 to 10 carbon atoms in the alkyl moiety, copolymers of vinyl acetate with an alkyl acrylate having 1 to 10 carbon atoms in the alkyl moiety and vinyl acetate-ethylene copolymers.

6. A pressure-sensitive adhesive tape or sheet as claimed in claim 1 in which said adhesive composition is prepared by homogeneously blending said water-soluble polyol and said water-soluble or water-swellable polymer with an aqueous latex of said pressure-sensitive adhesive.

7. A pressure-sensitive adhesive tape or sheet as claimed in claim 1 wherein the water-soluble polyol (a) is glycerin, the water-soluble or water-swellable polymer (b) is polyvinyl alcohol, and the adhesive is a member selected from the group consisting of natural rubbers, grafted natural rubbers and cross-linked natural rubbers.

* * * * *

UNITED STATES PATENT OFFICE
CERTIFICATE OF CORRECTION

Patent No. 4,226,915          Dated October 7, 1980

Inventor(s) Eiji Iijima et al

It is certified that error appears in the above-identified patent and that said Letters Patent are hereby corrected as shown below:

Column 8, line 39; change "the weight" to ---the total weight---.

Column 8, line 42; after "on" insert ---human skin.---.

Signed and Sealed this

Third Day of February 1981

[SEAL]

Attest:

RENE D. TEGTMEYER

Attesting Officer     Acting Commissioner of Patents and Trademarks